United States Patent [19]

Tepper

[11] Patent Number: 5,607,300
[45] Date of Patent: Mar. 4, 1997

[54] REMOVABLE RESILIENT ORTHODONTIC RETAINER

[76] Inventor: Harry W. Tepper, 535 Ocean Ave. #2B, Santa Monica, Calif. 90402

[21] Appl. No.: 557,603

[22] Filed: Nov. 14, 1995

[51] Int. Cl.$^6$ .................................................. A61C 3/00
[52] U.S. Cl. ............................................. 433/6; 433/24
[58] Field of Search ............................ 433/6, 7, 18, 24

[56] References Cited

U.S. PATENT DOCUMENTS

| | | | |
|---|---|---|---|
| 1,582,570 | 4/1926 | Brust . | |
| 3,162,948 | 12/1964 | Gerber . | |
| 4,028,808 | 6/1977 | Schwartz . | |
| 4,299,568 | 11/1981 | Crowley | 433/6 |
| 4,416,626 | 11/1983 | Bellavia | 433/7 |
| 4,433,956 | 2/1984 | Witzig | 433/7 |
| 4,468,196 | 8/1984 | Keller | 433/24 |
| 4,976,614 | 12/1990 | Tepper | 433/18 |
| 5,096,416 | 3/1992 | Hulsink | 433/6 |
| 5,145,364 | 9/1992 | Martz et al. | 433/6 |
| 5,167,499 | 12/1992 | Arndt et al. | 433/7 |
| 5,203,695 | 4/1993 | Bergersen | 433/6 |
| 5,376,001 | 12/1994 | Tepper | 433/6 |
| 5,415,542 | 5/1995 | Kesling | 433/6 |

*Primary Examiner*—Nicholas D. Lucchesi
*Attorney, Agent, or Firm*—Gordon K. Anderson

[57] ABSTRACT

An orthodontic retainer which has an upper portion and a lower portion, with the upper defining an upper labial arch filament (20) positioned around anterior surfaces of a patient's teeth attached on each end to a pair of upper clasps (22). The clasps surround upper midregion teeth and are embedded into an upper lingual resilient thermoplastic bridge (32) that include a U-shaped posterior bridge integral with a palatal bridge leaving an open area (38) therebetween. The lower portion of the retainer utilizes a similar filament (40) and clasps (42) with the lower bridge (44) in horseshoe shape. The combined rigid clasps and resilient thermoplastic memory characteristics of the filament and bridges maintain a patient's tooth location and attitude. A second and third embodiment add resilient wire (46) at appropriate locations within the thermoplastic bridges (32) and (44) magnifying the memory characteristics of the retainer.

19 Claims, 2 Drawing Sheets

REMOVABLE RESILIENT ORTHODONTIC RETAINER

TECHNICAL FIELD

The present invention relates to orthodontic retainers in general. More specifically to removable retainers having resilient bridges and labial arches for holding teeth in position after correction.

BACKGROUND ART

Previously, many types of retainers have been used in endeavoring to provide an effective means for retaining a patient's teeth after orthodontic corrections of malocclusions have been made. Most of the prior art utilizes the same basic approach as the orthodontic appliance used to make the original rectification, as in most cases, the appliance is rigid and designed to place pressure at specific points and areas. The prior retainers utilized a combination of steel wire, springs and elastic bands, along with a thermoset plastic bridge most commonly using a hard acrylic, such as methyl methacrylate.

The Hawley retainer is well known in the art and has been in use for many years. This retainer consists of acrylic covering the full palate, along with the lingual mucosa area and is sometimes vented to expose selected palatal regions. While prior art has accomplished much using rigid materials, a search did not disclose any patents that rely upon resilient structure for retention, however, the following U.S. patents are considered related.

| U.S. Pat. No. | Inventor | Issue Date |
| --- | --- | --- |
| 5,376,001 | Tepper | Dec. 27, 1994 |
| 5,167,499 | Arndt et al | Dec. 1, 1992 |
| 5,096,416 | Hulsink | Mar. 17, 1992 |
| 4,976,614 | Tepper | Dec. 11, 1990 |
| 4,468,196 | Keller | Aug. 28, 1984 |
| 4,433,956 | Witzig | Feb. 28, 1984 |
| 4,416,626 | Bellavia | Nov. 22, 1983 |
| 4,028,808 | Schwartz | Jun. 14, 1977 |
| 3,162,948 | Gerber | Dec. 29, 1964 |
| 1,582,570 | Brust | Apr. 27, 1926 |

U.S. Pat. No. 5,376,001, issued to the present inventor, discloses a removable orthodontic appliance which utilizes a similar pair of clasps seated over midregion teeth connected to a labial arch wire. A pair of structural braces, either molded wings or connecting sections are attached to a radial loop of metal forming a palatial bridge. The loop preferably made of memory metal having the consistent tendency to return to its original state exerts persistent linear force in the opposite direction of deformation. The clasp is made of three pieces of tube and wire, and wings that are formed of rigid mono-methylate, which sets quickly under ultra violet light.

Arndt et al, in U.S. Pat. No. 5,167,499, disclose a removable orthodontic palatial expansion arch in an "M" shape of nickel titanium wire attached to a metal band surrounding the upper first permanent molars.

U.S. Pat. No. 5,096,416 of Hulsink teaches an orthodontic retainer made of hard non-moving acrylic sections interconnected by resilient wires. A spring arm made of acrylic covered wire engage the labial surfaces of the four front teeth. A pair of Adam's clasps supported by a rigid plate extend over the first molar assisting in clasping the retainer in place. It will be noted that all of the plates are rigid and the resiliency is provided by flexible wires.

U.S. Pat. No. 4,976,614, also issued to the present inventor, utilizes midregion clasps and a label filament serving as a reference arch, along with a curved lingual spring filament urging the teeth against the reference. Synthetic resin filaments of transparent material hold the teeth to prevent relapse. A sinuous palatal arch wire, continuous in form, but having cyclic variations, extends across the patient's palate and provides a spreading force upon clasps attached to opposed pre-molar or bicuspid teeth. In another embodiment opposed facing palatal wings of hard material encompass the gingival region of a number of molars and include a wire arch device which extends back across the roof of the patient's mouth.

Keller's U.S. Pat. No. 4,468,196 employs a method of treatment and an apparatus which includes bands around selected molars and an arch wire with springs that exert a specific force. A bracing wire is placed in contact with the buccal surfaces of the front teeth and is covered with a hardenable acrylic.

Witzig, in U.S. Pat. No. 4,433,956, employs acrylic anterior segments over the front teeth in conjunction with an expandable screw, connecting a similar posterior segment over the mid-range teeth. The appliance is adjusted in stages to correct lower jaw movements.

U.S. Pat. No. 4,416,626, issued to Bellavia, teaches a method and apparatus which utilizes acrylic wings with caps that cover screw adjusting mechanisms and alignment pins.

For background purposes and as indicative of the art to which the invention is related, reference may be made to the patents issued to Schwartz, Gerber and Brust.

DISCLOSURE OF THE INVENTION

The field of orthodontic appliances and retainers is replete with structure using wires, bands, clasps, springs, screw adjustments, bridges, and the like, for holding teeth and creating movement. In some cases, the appliance is attached to the patient's teeth directly and stays in place until the malocclusion is corrected. Other appliances are removable and adjustments are made over periods of time to complete the correction. In order to prevent relapse when the orthodontic treatment is concluded, a retainer is worn by the patient. As previously discussed, retainers include a lingual portion that is custom fit to generally engage the undercuts of the teeth, and wire members are embedded to coact with the teeth for securement. The most widely used appliance of this type is known as the Hawley retainer and, along with it, variations are constructed of a hard unyielding acrylic and act as a rigid barrier. It has been known that this popular retainer has had some asperity in fabrication, as removal from the model has proven difficult due to the hard nature of the acrylic. It is, therefore, a primary object of the invention to, not only overcome this difficulty in fabrication, but to add an entirely new aspect to retainers in general. The present invention utilizes an injection molded thermoplastic as the material for the bridge structure. This novel approach now creates an appliance that actually exerts a gentle but constant force on only the teeth that have the tendency to revert from their final corrected position. A labial arch filament that is registered around the anterior teeth provides the limit position and a bridge of resilient thermoplastic is in intimate contact with the undercuts of all of the representative teeth providing control that has infinite memory and, yet, is flexible enough to be comfortable and utilitarian. Clasps of a memory metal apply tension on the labial arch filament, which by itself is a flexible thermoplastic. The retainer, or positioner, now places pressure only where required and may be worn with ease for long periods of time, including eating meals.

An important object of the invention is the ability to make minor tooth movements including rotations and even bodily movements by simply correcting the inaugural plaster cast by removing and resetting the image to the desired position and recasting the mold. This flexibility permits a broad spectrum of corrections to be made with little effort and the memory characteristics of the resilient thermoplastic provides the needed constant force.

Another object of the invention is directed to the labial arch filament, which may be transparent and hardly visible at a distance. This cosmetic effect has a desired appeal for many, or on the other hand, the arch filament may be colored brightly for those desiring novelty.

Still another object of the invention is the open palatal area of the upper portion of the retainer. By having the roof of the patient's mouth open, proper proprioceptive tongue posture is realized. Further, wearing the retainer during eating is not only possible, but tongue function is enhanced due to the complete lack of obstruction to the palatal rugae region and minimal contact with the mucosal tissue.

Yet another object of the invention is the lack of physical weight of the appliance, as it is thin and formed of relative light components, therefore, the combined device has little weight which adds considerably to the comfort of the patient when wearing the device.

A further object of the invention has to do with the basic materials, which individually are not toxic and are allergy free. All materials used in the invention have already been cleared by the Food and Drug Administration for similar applications.

A final object of the invention is the use of a two-piece clasp bracket that is unique and novel in its own right. The clasp is made of only two pieces of wire that are brazed together with cadmium free silver solder. This clasp consists of an omega loop wire and a marginal ridge wire with the loop flattened on one end. The marginal ridge wire is rectangularly formed with the exposed ends opposed and may be used as clamps or levers. The clasp is fabricated in the flat and the dental technician may then individually form the assembly into the configuration required, right or left hand, including rolling the flattened end of the loop into a filament receiving circular ring. This construction technique simplifies fabrication of the appliance, as clasps may be mass produced on wire forming equipment, thus reducing the labor content of the dental practitioner and overall expense.

These and other objects and advantages of the present invention will become apparent from the subsequent detailed description of the preferred and other embodiments, also the appended claims, further taken in conjunction with the accompanying drawings.

BEST MODE FOR CARRYING OUT THE INVENTION

The best mode for carrying out the invention is presented in terms of a preferred, second and a third embodiment. All three embodiments are primarily designed alike, except the second and third have added structure to the basic preferred embodiment.

The preferred embodiment, as shown in FIGS. 1 through 8, comprises an orthodontic retainer for both the upper and lower dental arches to be used in concert, or singly if the occasion arises. The upper portion of the retainer is illustrated in FIGS. 1, 3, 5 and 6 and consists of an upper labial arch filament 20 that is contiguous with the labial surfaces of the patient's upper anterior teeth for creating a limiting position. The filament 20 is made of a thermoplastic material having a relative high tensile yield strength. While any thermoplastic filament having the requisite characteristics may be used, it has been found that a nylon formulated of hexametylenediamine and dodecanedioic acid, as manufactured by DuPont under the designation nylon 612 and registered tradename TYNEX is ideal. The nylon filament 20 may be utilized in this invention in its transparent form or may be colored a variety of bright hues, which may be attractive to the younger patient wearing the retainer.

Figure 1:
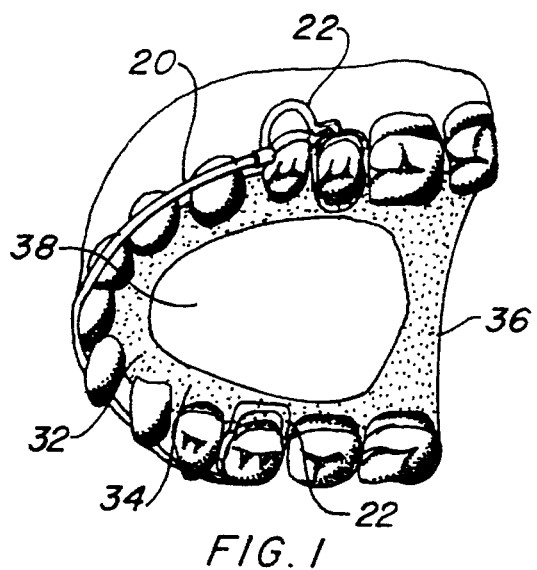
FIG. 1 is a partial isometric view of the upper orthodontic retainer portion viewed from beneath.
Figure 2:
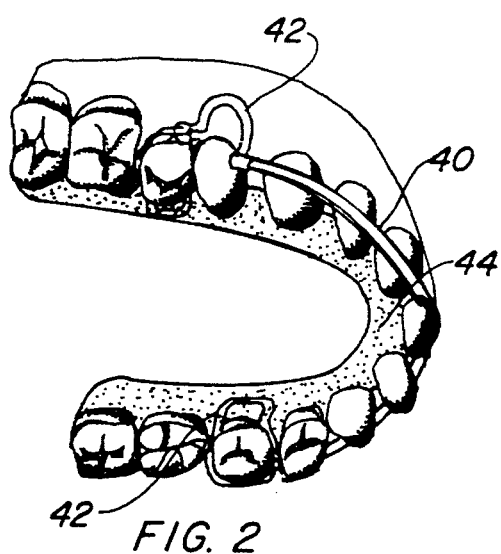
FIG. 2 is a partial isometric view of the lower orthodontic retainer portion viewed from above.
Figure 3:
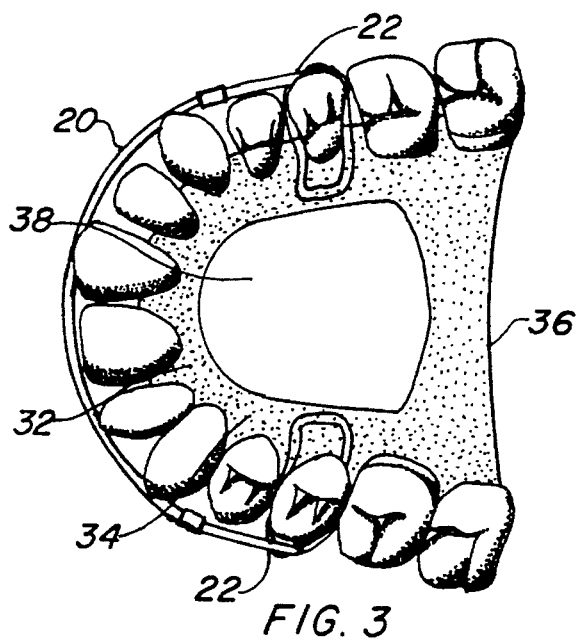
FIG. 3 is a plan view of the upper orthodontic retainer.
Figure 4:
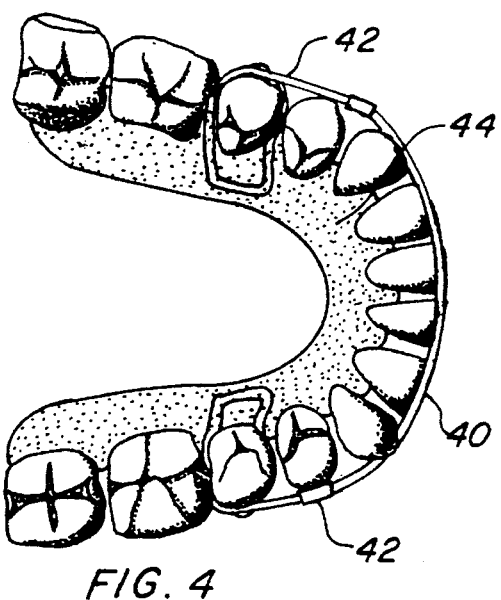
FIG. 4 is a plan view of the lower orthodontic retainer.
Figure 5:
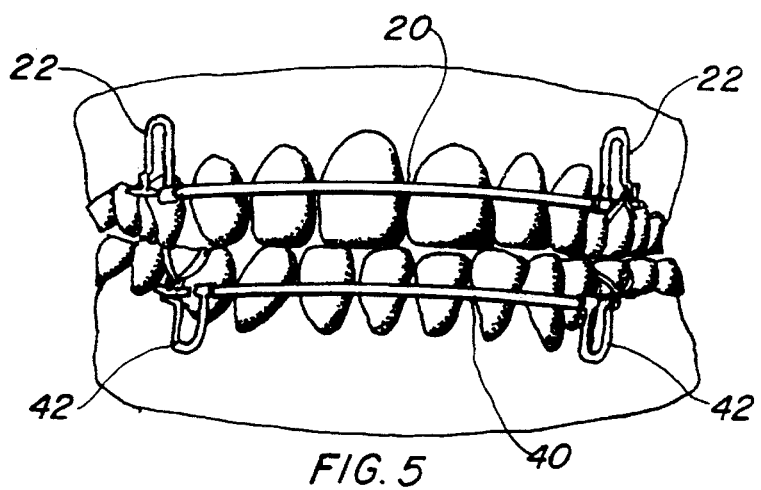
FIG. 5 is a front view of the complete retainer attached to a patient's teeth.
Figure 6:
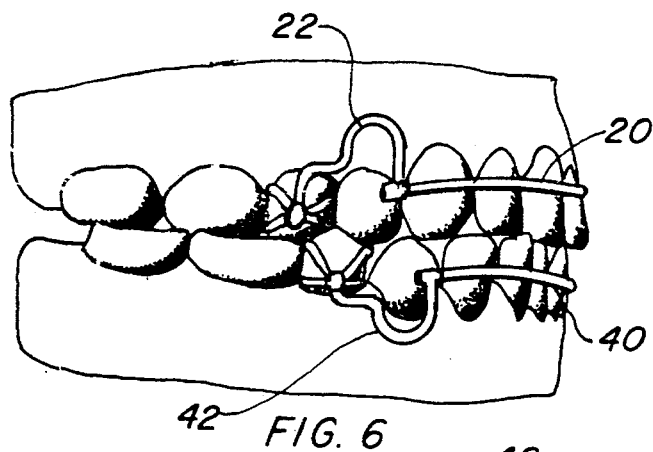
FIG. 6 is a right side view of the complete retainer attached to a patient's teeth.

A pair of upper clasps 22 secure the filament 20 at each end. These clasps 22 removably engage the upper midregion teeth on opposite sides, as shown in FIGS. 1, 3 and 5. The exact attaching tooth may vary as to the individual patient's requirements, however, the drawings illustrate the second bicuspids. The clasp 22 in this combination is unique in and of itself, as it may be mass produced in the flat and formed into shape by the dental practitioner at the time of fabrication. It will be noted that the present inventor has already applied for a separate design patent for the clasp in the flat and it is presently pending under Ser. No. 29/043,770. The clasp 22 is shown in the flat in FIG. 7 and formed into the final usable shape in FIG. 8. Each clasp 22 consists of a marginal ridge wire 24 that is formed into a rectangular shape with upper end segments bent angularly inward until they almost touch and then sharply bent outwardly in opposed directions, thus forming a T-shape on top. An omega loop wire 26 is formed in a "U" like loop shape described as having a first end and a second end for clarity. The first end is depicted on the left and has a right angle step downward. The second end also distends downwardly from the loop and is flattened 28 on the terminating end. The two elements are aligned, with the second end of the loop 26 disposed contiguously between the inwardly bent portions of the marginal ridge wire 24. The intersecting joint is brazed with cadmium free silver solder 30, preferably 45/30/25 alloy per Federal standard QQ-B-654. The above wires 24 and 26 are preferably stainless steel, however, other wire materials may be substituted with equal ease.

Figures 7, 8:
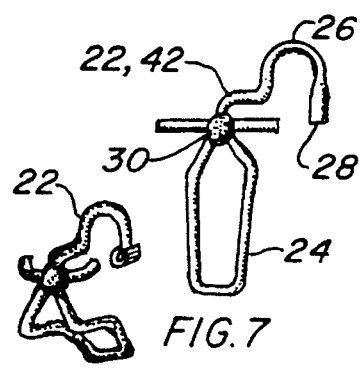
FIG. 7 is a front view of the clasp in the flat completely removed from the invention for clarity.
FIG. 8 is a partial isometric view of the clasp bent into a right hand configuration for an upper retainer.

FIG. 8 depicts one configuration of the clasp 22 with the flattened end 28 of the loop wire 26 rolled into a cylindrical shape to receive the labial arch filament 20. The clasp is bent to surround the appropriate tooth with the rectangular end of the ridge wire 24 conforming to the slope of the patient's adjacent mucosal tissue. It should be noted that the final shape will differ considerably, as each clasp must be custom fit to accommodate the patient's oral configuration.

The upper clasps 22 are joined together with upper lingual resilient thermoplastic bridge means 32, which comprise a U-shaped posterior bridge 34 from lingual surfaces of a patient's mucosal tissue and teeth up to and including second molars, when present. This bridge 34 is formed integrally with a posterior palatal bridge 36 that spans the patient's palatal arch region. An open area 38, surrounded by these bridges 34 and 36, circumvents the patient's palatal regae region allowing proper proprioceptive tongue position relative to the rugae. The open area 38 also permits greater lateral and longitudinal flexibility of the retainer.

The configuration and attaching points of the clasps 22 embedded into the bridge means 32 maintain the patient's tooth location and attitude by the combined effort of the rigidly attached clasps 22 and the memory characteristics of the resilient thermoplastic bridge means 32, as previously discussed. In order to achieve the most notable results, the resilient thermoplastic must have substantial memory and structural integrity to accomplish the retaining ability and minor rotations and bodily movement built into the appliance. There are many resilient thermoplastic materials that meet the design criteria, such as a formulation of polybisphenol-A carbonate, manufactured by General Electric under its tradename LEXAN, or Mobay Chemicals under its tradename MERLON, which has been found to be the forerunner material. Hexametylenediamin and dodecanedioic acid manufactured by DuPont et al under the generic name nylon is also acceptable, along with a proprietary material manufactured by, and designated, VAL-PLAST. Other materials include a combination of polybisphenol-A carbonate and hexametylenediamine with dodecanedioic acid (nylon) and also a natural based thermoplastic of vulcanized rubber. Still other resilient thermoplastics include solid polyurethane elastomers produced by numerous manufacturers, such as Stevens Molded Products, under their registered trademark HI-TUFF and many others.

The upper bridge means 32 is constructed using the well known and popular injection molding process applying the so-called last wax procedure for developing the mold. The thermoplastic, in granular form, is heated to plasticity in a cylinder, then forced through sprues and runners into a controlled temperature mold, forming the bridge with the clasps 22 embedded at the appropriate location. This procedure leaves the bridge finished with no polishing or trimming necessary. As previously mentioned, easy modifications in the original plaster cast permit the final configuration to include the corrections needed to apply pressure from the resilient material to straighten or move teeth, as required.

The lower portion of the orthodontic retainer is depicted in FIGS. 2, 4 through 6, and is basically the same as the upper portion. A lower labial arch filament 40 is of the same material and is registered about the lower labial anterior teeth surfaces in the same manner. Each lower clasp 42 is identical to start with, in the flat, as shown in FIG. 7, however, it is bent into a reverse image for the lower connection to the teeth and bridge. The lower lingual resilient thermoplastic bridge 44 is joined to the lower clasps 42 and is in a horseshoe shape. As with the bridge means 32, the lower bridge 44 proceeds around the lingual surfaces of the patient's mucosal tissue and teeth up to and including second molars, when present. The materials of both the lower filament 40 and lower bridge 44 are the same as their corresponding elements 20 and 32.

Figure 9:
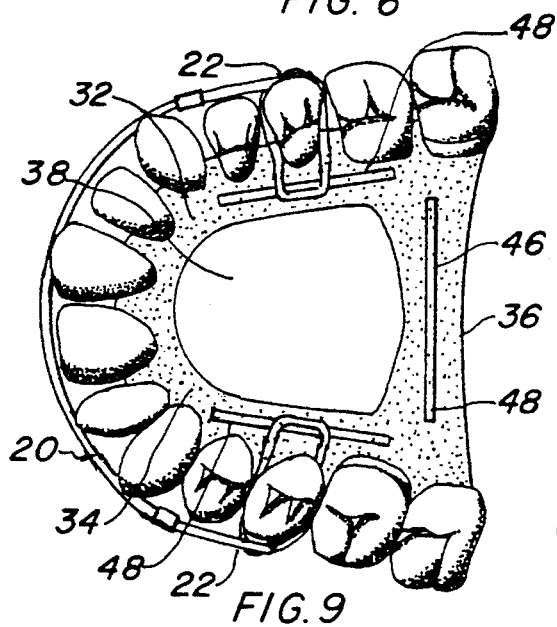
FIG. 9 is a plan view of the second embodiment of the retainer upper portion orthodontic retainer with the straight wires embedded in the bridge.
Figure 10:
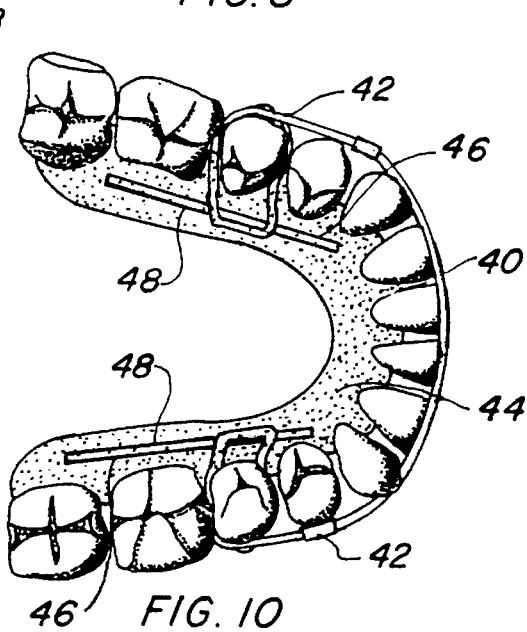
FIG. 10 is a plan view of the second embodiment of the retainer lower portion orthodontic retainer with the straight wires embedded in the bridge.

The second embodiment is depicted in FIGS. 9 and 10 and differs only in the addition of at least one resilient wire 46 embedded in the upper and lower portion of the retainer. Specifically, the upper portion illustrated in FIG. 9, preferably includes three separate straight wire segments 48, a pair of segments 48 parallel the patient's teeth on each side and an arched segment across the palatial bridge. While these are designated "straight", they may be arched to follow the contour of the bridge and, yet, are straight in one plane, as shown. The lower portion, likewise, includes a pair of straight segments 48 embedded on opposed sides between the patient's second molars and up to cuspids.

Figure 11:
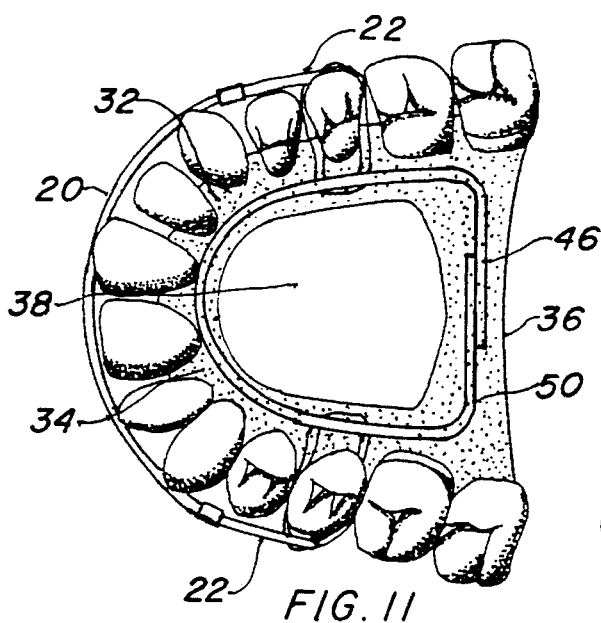
FIG. 11 is a plan view of the third embodiment of the retainer upper portion orthodontic retainer with a single wire segment embedded in the bridge.
Figure 12:
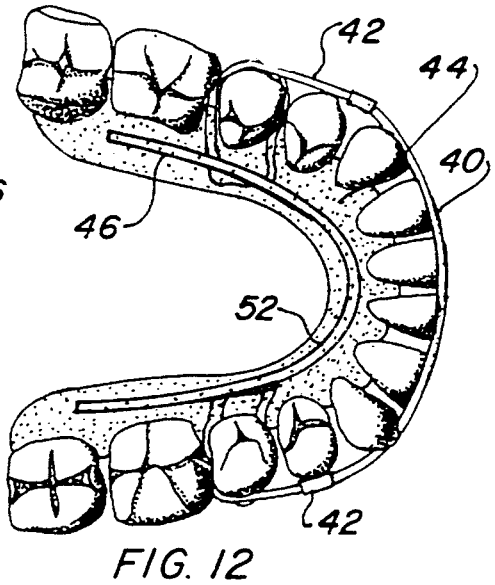
FIG. 12 is a plan view of the third embodiment of the retainer lower portion orthodontic retainer with a single wire segment embedded in the bridge.

The third embodiment is depicted in FIGS. 11 and 12 and basically includes at least one resilient wire 46 embedded in each upper and lower portion of the retainer. The upper portion, shown in FIG. 11, employs a single wire segment 50 bent to follow the contour of the patient's teeth and arch across the palatal bridge 36. While the single wire segment 50 is shown terminating by overlapping on the bridge 36, the joint may be at any convenient location and either overlap, butt, or be spaced apart, as desired. The lower retainer includes a U-shaped segment 52, depicted in FIG. 12, that follows the patient's lower teeth contour.

In each case the wire 46 is embedded completely into the bridge 32 or 44 and may be positioned underneath the clasps 22 and 42, as shown in FIGS. 9 and 10, or on top of the clasps, illustrated in FIGS. 11 and 12, or any combination thereof with equal ease.

The wire 46, in all its variations, is added to the upper and lower retainer portions for augmenting the propensity of each bridge to return to its original posture, or memory, thus maintaining a patient's tooth location and attitude by combining the resilient thermoplastic memory characteristics of the bridge structure 32 and 44 with the stiffness or resiliency of the wire 46.

The wire 46, in all of its different segments 48, 50 and 52, may be made of a variety of different materials, all functioning properly, but each having slight variations in its flexing characteristics. Stainless steel, so-called "KANGAROO" steel, ferrous metal and nickel titanium in a diameter of from 0.010 inch (0.254 mm) to 0.050 inch (1.27 mm) are all acceptable wire materials and sizes. It has been found, however, that nickel titanium wire of 0.028 inch (0.71 mm) to 0.036 inch (0.91 mm) in diameter is the preferred selection for most common applications.

While the invention has been described in complete detail and pictorially shown in the accompanying drawings, it is not to be limited to such details, since many changes and modifications may be made in the invention without departing from the spirit and scope thereof. Hence, it is described to cover any and all modifications and forms which may come within the language and scope of the appended claims.

What is claimed is:

1. An improved removable resilient orthodontic retainer for upper and lower dental arches comprising:

an upper labial arch filament registrable about labial surfaces of upper anterior teeth to define a limit position, the upper labial arch filament being of a thermoplastic material, a pair of upper clasps removably engagable to upper midregion teeth on opposite sides and secured to the upper labial arch filament at each end thereof, upper lingual resilient thermoplastic bridge means joined to the upper clasps having a combined U-shaped posterior bridge adapted to extend from lingual surfaces of patient's mucosal tissue and teeth up to and including second molars, when present, and an integral posterior palatal bridge adapted to span a patient's palatal arch region, the bridge means defining an open area adapted to circumvent a patient's palatal rugae region, the upper retainer portion adapted to maintain the patient's tooth location and attitude by combined rigid clasps and resilient thermoplastic memory characteristics, a lower labial arch filament registrable about lower labial anterior teeth surfaces to define a limit position, the lower labial arch filament being of a thermoplastic material, a pair of lower clasps removably engagable to lower midregion teeth on opposite sides and secured to the lower labial arch filament at each end thereof, and a lower lingual resilient thermoplastic bridge joined to the lower clasps defining a horseshoe shaped posterior bridge adapted to extend from lingual surfaces of patient's mucosal tissue and teeth up to and including second molars, when present, maintaining patient's tooth location and attitude by combined rigid clasps and resilient thermoplastic memory characteristics.

2. The orthodontic retainer as recited in claim 1 wherein said upper and lower labial arch filaments are transparent.

3. The orthodontic retainer as recited in claim 1 wherein said upper and lower labial arch filaments are colored.

4. The orthodontic retainer as recited in claim 1 wherein said upper and lower labial arch filament thermoplastic material further comprises hexametylenediamine and dodecanedioic acid.

5. The orthodontic retainer as recited in claim 1 wherein said upper and lower clasps further comprise;

a marginal ridge wire formed rectangularly with end segments bent angularly inward, almost touching and outwardly opposed in a T-shape, an omega loop wire in a "U" shaped loop shape having a first end and a second end with the first end formed into a right angle step and the second end distending from the loop and flattened forming a circular loop for retaining the labial arch filament, and a brazed joint of cadmium free silver solder joining the marginal ridge wire and the omega loop wire at the inward bend of the ridge wire and the first end of the loop wire, the entire clasp further bent to fit individual patient's teeth and a rectangular end of each ridge wire embedded in a respective bridge.

6. The orthodontic retainer as recited in claim 5 wherein said marginal ridge wires and omega loop wires are stainless steel.

7. The orthodontic retainer as recited in claim 1 wherein said upper bridge means and lower bridge thermoplastic further comprise polybisphenol-A carbonate.

8. The orthodontic retainer as recited in claim 1 wherein said upper bridge means and lower bridge thermoplastic further comprise hexametylenediamine and dodecanedioic acid.

9. The orthodontic retainer as recited in claim 1 wherein said upper bridge means and lower bridge thermoplastic further comprise a combination of polybisphenol-A carbonate and hexametylenediamine with dodecanedioic acid.

10. The orthodontic retainer as recited in claim 1 wherein said upper bridge means and lower bridge thermoplastic further comprise vulcanized rubber.

11. The orthodontic retainer as recited in claim 1 wherein said upper bridge means and lower bridge thermoplastic further comprise polyurethane.

12. The orthodontic retainer as recited in claim 1 further comprising at least one resilient wire embedded within the upper bridge means and lower bridge to parallel with a patient's teeth and across the palatal bridge for augmenting the propensity of each of said upper bridge means and said lower bridge to return to its original posture, thus magnifying the memory characteristic of the retainer.

13. The orthodontic retainer as recited in claim 12 wherein said resilient wires are stainless steel.

14. The orthodontic retainer as recited in claim 12 wherein said resilient wires are ferrous metal.

15. The orthodontic retainer as recited in claim 12 wherein said resilient wires are nickel titanium metal.

16. The orthodontic retainer as recited in claim 12 wherein said resilient wires are from 0.010 inch (0.254 mm) diameter to 0.050 inch (1.27 mm) diameter.

17. An improved removable resilient orthodontic retainer for upper and lower teeth comprising:

an upper labial arch filament registrable about upper anterior teeth surfaces to define a limit position, the upper labial arch filament being of a thermoplastic material, a pair of upper clasps removably engagable to upper midregion teeth on opposite sides and secured to the upper labial arch filament at each end thereof, upper lingual resilient thermoplastic bridge means joined to the upper clasps having a combined U-shaped posterior bridge adapted to extend from lingual surfaces of patient's mucosal tissue and teeth up to and including second molars, if present, and an integral posterior palatal bridge adapted to span a patient's palatal arch region, the bridge means defining an open area adapted to circumvent a patient's palatal rugae region, at least one resilient wire embedded within the upper bridge means adapted to extend parallel to patient's teeth and across the palatal bridge for augmenting the propensity of the bridge means to return to its original posture maintaining a patient's tooth location and attitude by combined resilient thermoplastic memory characteristics of the bridge structure and embedded wire, a lower labial arch filament registrable about lower anterior teeth surfaces to define a limit position, the lower labial arch filament being of a thermoplastic material, a pair of lower clasps removably engagable to lower midregion teeth on opposite sides and secured to the lower labial arch filament at each end thereof, a lower lingual resilient thermoplastic bridge joined to the lower clasps defining a horseshoe shaped posterior bridge adapted to extend from lingual surfaces of patient's mucosal tissue and teeth up to and including second molars, if present, and at least one resilient wire embedded within the lower bridge adapted to extend parallel to patient's teeth for augmenting the propensity of the bridge to return to its original posture, maintaining a patient's tooth location and attitude by combined resilient thermoplastic memory characteristics of the bridge structure and embedded wire.

18. The orthodontic retainer as recited in claim 17 wherein said resilient wire embedded within the upper bridge means further comprises a pair of straight wire segments adapted to extend parallel with patient's teeth, one on each side, and an arched segment across the palatal bridge, and said resilient wire embedded within the lower bridge further comprises a pair of straight segments adapted to be disposed between patient's second molars and up to cuspids.

19. The orthodontic retainer as recited in claim 17 wherein said resilient wire embedded within the upper bridge means further comprises a single wire segment bent to follow a patient's teeth and arched across the palatal bridge, and said resilient wire embedded within the lower bridge further comprises a U-shaped segment adapted to follow a patient's lower teeth contour.

* * * * *